United States Patent [19]

Janke et al.

[11] Patent Number: 5,207,637
[45] Date of Patent: May 4, 1993

[54] HINGED CAGE-TYPE KNEE BRACE

[75] Inventors: Wayne R. Janke, Pasadena; Dan J. Edwards, Sunland, both of Calif.

[73] Assignee: United States Manufacturing Company, Pasadena, Calif.

[21] Appl. No.: 903,780

[22] Filed: Jun. 24, 1992

[51] Int. Cl.$^5$ ............................................. A61F 5/00
[52] U.S. Cl. ........................................ 602/26; 602/16
[58] Field of Search ................... 602/26, 5, 23, 16, 15; 128/80; 623/38, 39, 28, 27

[56] References Cited

U.S. PATENT DOCUMENTS 4,372,298  2/1983  Lerman ................................. 602/26
5,133,341  7/1992  Singer et al. ......................... 602/16

OTHER PUBLICATIONS

Hans Richard Lehneis, C.P.O., "The Swedish Knee Cage," Reprinted from *Artificial Limbs*, vol. 12, No. 2, pp. 54–57.

Primary Examiner—Richard J. Apley
Assistant Examiner—B. Meinol
Attorney, Agent, or Firm—Christie, Parker & Hale

[57] ABSTRACT

A knee brace includes a cage-type frame formed as a rigid unit and having upper lateral and medial uprights, lower lateral and medial uprights, and a generally U-shaped fixed posterior brace that extends behind the knee. The pairs of upper and lower uprights extend along upper and lower lateral and medial sides of the upper and lower leg, respectively, above and below the knee joint. Long lateral and medial pivot arms are hinged to the upper lateral and medial uprights, respectively, and these pivot arms hold upper and intermediate flexible straps releasably securing the upper portion of the brace to the thigh well above the knee joint. A flexible lower strap affixed to the lower uprights releasably secures the lower portion of the brace to the patient's lower leg. A flexible U-shaped posterior strap affixed adjacent the knee joint extends behind the knee joint to controllably restrict hyperextension. The hinged connection of each pivot arm to its corresponding upright allows the upper portion of the brace with its upper and intermediate straps to be releasably secured to the thigh so that the upper portion of the brace rotates with a normal walking gait. Rotational stops at the lateral and medial pivot joints limit rotation to restrict hyperextension. These pivot joints include noise-free bushings. The pivot joints are spaced a short distance above the knee joint axis to improve cosmetics. The hinged portions of the brace functionally distribute thigh forces as well as avoiding slippage of the brace during use.

9 Claims, 8 Drawing Sheets

HINGED CAGE-TYPE KNEE BRACE

FIELD OF THE INVENTION

This invention relates to knee braces, and more particularly, to an improved knee brace for supporting the knee to prevent hyperextension of the knee joint while allowing the knee joint to otherwise bend safely about a horizontal axis through the knee. More particularly, the invention has to do with an improvement to a knee brace commonly known as a Swedish knee cage.

BACKGROUND OF THE INVENTION

Certain types of knee braces are worn by persons who suffer knee instabilities. If the patient's problem is genu recurvatum with minimal need for mediolateral stabilization, the knee orthosis can be simple and light in weight. The knee brace known in the art as a Swedish knee cage is an example of this type of orthosis. The Swedish knee cage has been used for many years and is good at restricting hyperextension of the knee by means of two anterior straps spaced above and below the knee joint and one U-shaped posterior strap held behind the knee joint. The knee cage is a rigid metal frame having a U-shaped bar extending behind the U-shaped anterior strap and a pair of upper and lower uprights on opposite sides of the frame which hold the upper and lower anterior straps. The Swedish knee cage provides a fixed three-point means of support intended to allow almost complete range of knee flexion, while the lateral and medial uprights provide a limited degree of mediolateral stability.

A principal objection to the Swedish knee cage is its lack of a cosmetic design. When the patient sits, the upper pair of uprights project well above the level of the knee, which can be unsightly since they protrude in an unnatural working way from the insides of the patient's clothes.

Another objection to the Swedish knee cage is that the cage, having minimal means of support on the leg, can slip or move up and down during use, which can be uncomfortable for the user.

An alternative design to the Swedish knee cage is a "three-way knee stabilizer" sold by Rehabilitation Technical Components, Inc. of Hillside, N.J. This device has pivotable strap attachments which make the device more cosmetic.

The present invention overcomes the cosmetic problems of the Swedish knee cage while providing a cage-type brace that prevents hyperextension of the knee. In addition, certain functional improvements not found in the standard Swedish knee cage or the three-way knee stabilizer are provided by the knee brace of this invention.

SUMMARY OF THE INVENTION

Briefly, the knee brace of this invention, in one embodiment, includes a cage-type frame formed as a rigid unit and having a pair of relatively short upper lateral and medial uprights for extending in a fixed position along the sides of the upper leg above the knee joint, together with a pair of relatively longer lower lateral and medial uprights for extending in a fixed position along the sides of the lower leg below the knee joint. The cage also includes a generally U-shaped fixed posterior brace for extending behind the knee joint, generally at the level of the knee joint axis of rotation. A pair of long rigid upper lateral and medial pivot arms are hinged to the short upper lateral and medial uprights, respectively. The pivot arms extend along the sides of the upper leg for a distance sufficient to hold a pair of flexible upper and intermediate leg straps for releasably securing the upper pivot arms to the thigh region, well above the knee joint. A flexible lower leg strap affixed to the lower lateral and medial uprights releasably secures the lower portion of the brace to the calf region of the patient's lower leg. A flexible U-shaped posterior strap is affixed to the cage adjacent the knee joint and extends behind the knee joint to restrict hyperextension of the knee. The hinged pivot joint connection of each pivot arm to its corresponding short upright includes a pivot spaced a short distance above the axis of the knee joint for shortening the fixed portion of the cage that projects above the knee joint axis of rotation. The long pivot arms that hold the upper and intermediate leg straps provide a means for distributing upper thigh forces. This allows a more normal walking gait during use, as well as providing more stabilized support for the knee. The pivot joints include rotational stops that limit hyperextension. The stops can include noise-free bushing inserts that produce a quiet rocking motion during use.

The brace of this invention effectively prevents knee hypertension while overcoming the cosmetic problems of the Swedish knee cage. The brace also allows a more natural motion of the knee and is more comfortable for the user in that it prevents the knee cage from slipping or moving up or down during use. In addition, the functional distribution of thigh forces allows the brace to be used as more of a functional brace, in the rehabilitation process, as opposed to the more passive Swedish knee cage type of brace.

These and other advantages of the invention will be more fully understood by referring to the following detailed description and the accompanying drawings.

DETAILED DESCRIPTION

Figure 1:
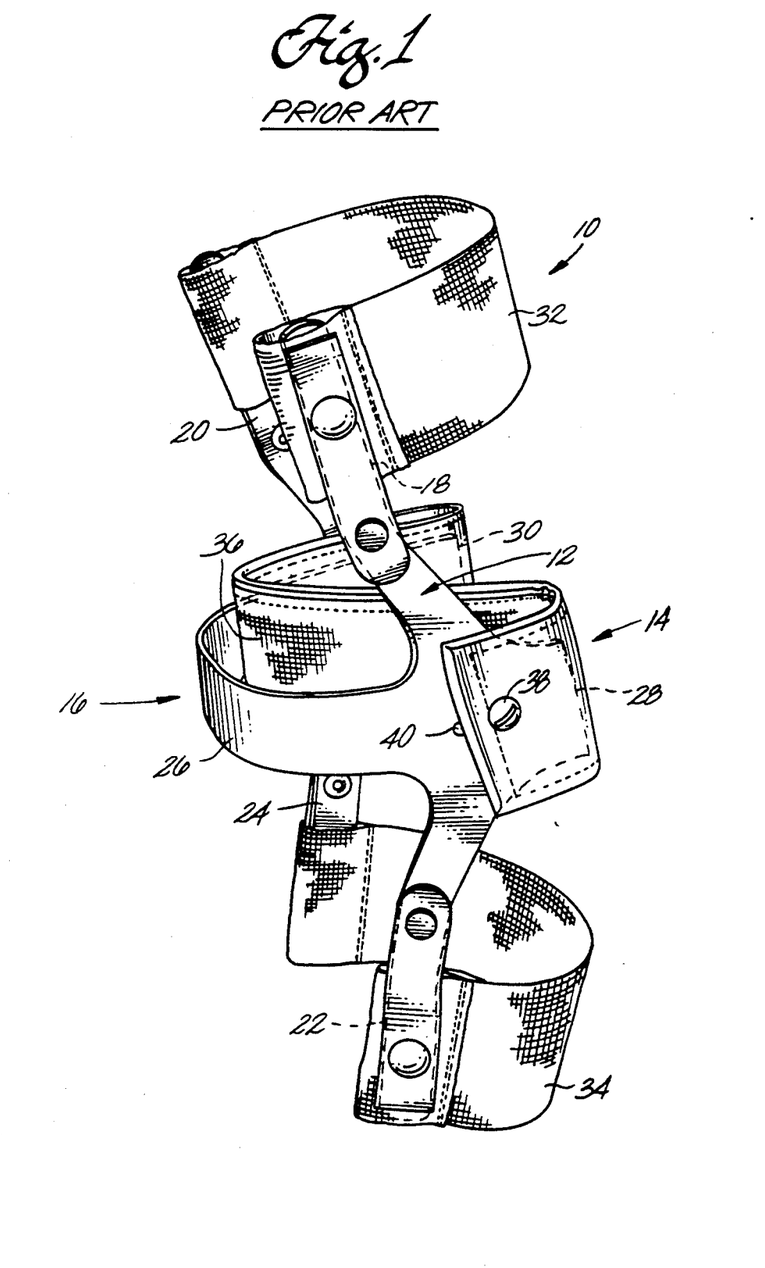
FIG. 1 is a perspective view showing a prior art standard Swedish knee cage.

To better appreciate the improvements provided by this invention, FIG. 1 illustrates a standard prior art knee brace 10 known as a Swedish knee cage. The brace includes a rigid metal frame or cage 12 having a front side 14 and a rear side 16. A pair of long, narrow upper lateral and medial uprights 18, 20 extend upwardly from the center of the brace. A pair of long, narrow lower lateral and medial uprights 22, 24 extend down from the center of the brace. In use, the upper lateral and medial uprights extend along the lateral and medial sides of the upper leg or thigh immediately above the knee joint. The lower lateral and medial uprights extend along lateral and medial sides of the lower leg or calf region of the leg immediately below the knee joint. The cage-like frame also includes a forwardly opening generally U-shaped rigid bar 26 at the center of the brace for extending in a generally horizontal position behind the knee joint. The U-shaped bar adds rigidity to the cage structure. A pair of flat, wide lateral and medial flanges 28, 30 project forward at the front of the cage, at the open ends of the U-shaped bar.

The uprights and U-shaped bar portion of the rigid cage are all of narrow cross section, approximately one-fourth inch in thickness. The vertical dimension or width of the U is about one inch, and the front flanged portion of the cage is about one and one-half inches wide in its vertical dimension. The uprights are each about five-eights inch wide. The upper pair of uprights are about four and one-fourth inches long, from their juncture at the wide front flanged portion of the cage. The lower pair of uprights also are about four and one-forth inches long in the opposite direction. Approximately the lower half of the upper pair of uprights extends rearwardly at an angle to an obtuse angular bend, leaving approximately the upper half of each upright to extend in a more upright but still angularly inclined position away from the front of the cage. The lower pair of uprights have a similar configuration.

A U-shaped flexible upper anterior strap 32 is secured to the upper ends of the upper pair of short uprights. Similarly, a U-shaped flexible lower anterior strap 34 is secured to the lower ends of the lower pair of long uprights. A U-shaped flexible posterior strap 36 is affixed at its ends to the flanged front portions of the cage. The outer ends of the posterior strap are releasably secured to the front of the cage by fasteners 38. The posterior strap wraps around the front flanged region of the cage and with a reverse bend extends in a U towards the rear inside of the cage, in front of the U-shaped bar 26. Spaced apart fastener holes 40 on the flanged lateral and medial front portions of the cage receive the fasteners 38 to adjust the depth of the U-shaped strap within the cage. The upper and lower anterior straps are each releasably secured to the upper and lower pairs of uprights, respectively, in a well known manner.

Generally speaking, the Swedish knee cage has been used in the past to control knee instabilities by restricting hyperextension by means of the two anterior straps extending across the front of the upper and lower leg, with the posterior strap extending behind the knee joint. This brace is a passive three-point knee stabilizer that is simple and light, but it has several disadvantages. The pair of upper uprights 18 and 20 extend a substantial distance above the knee joint axis in order to provide a rigid support for holding the upper anterior strap 32. When the user sits, the upper pair of uprights poke through the user's clothes, or otherwise project well beyond the user's upper leg, and therefore the brace has always been cosmetically undesirable. In addition, the brace is prone to slippage and can interfere with a comfortable normal walking gait.

Figure 2:
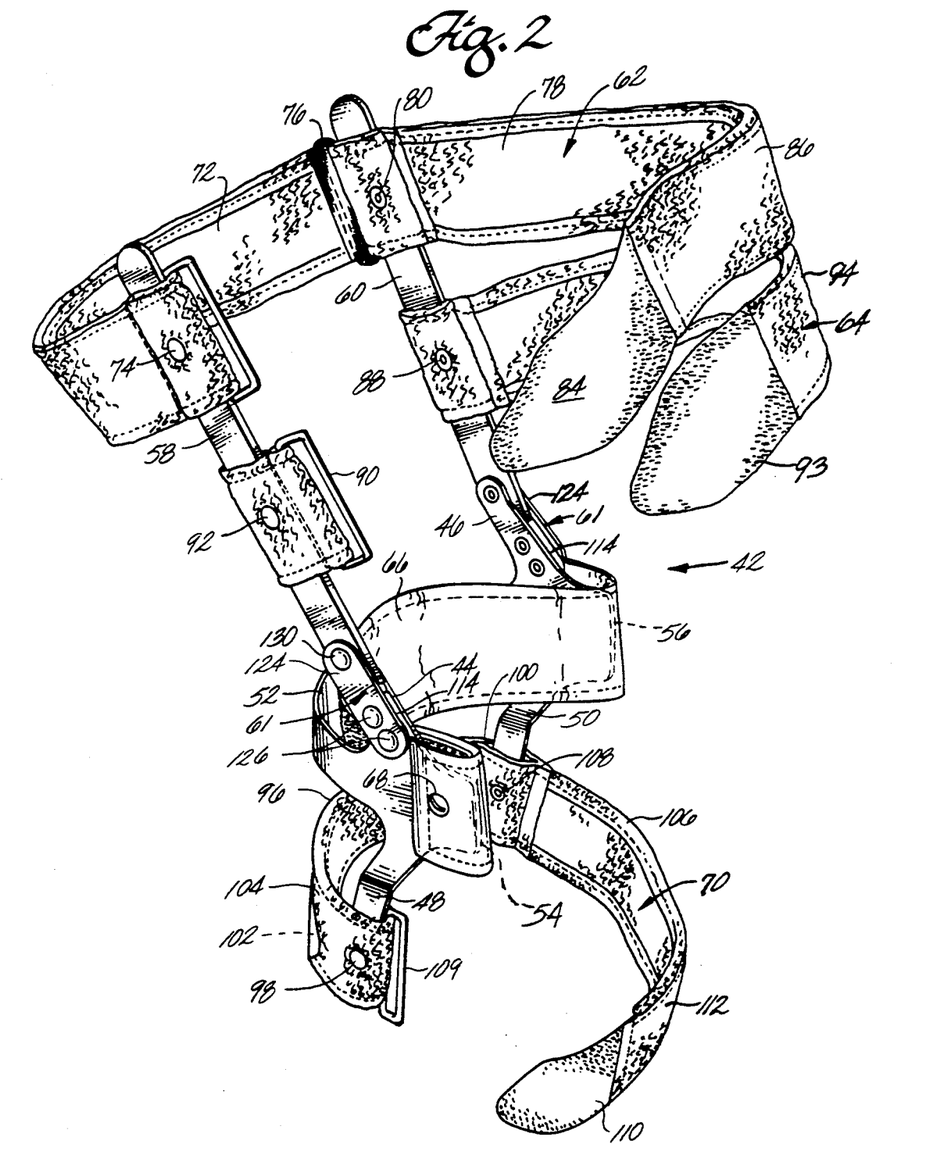
FIG. 2 is a perspective view showing an improved cage-type knee brace according to principles of this invention.

FIG. 2 is a perspective view illustrating a cage-type knee brace 42 of this invention which provides knee stabilization and prevents knee hyperextension similar to the Swedish knee cage, while overcoming problems characteristic of the Swedish knee cage. The brace also provides functional advantages, described below, not available with the standard Swedish knee cage. The improved brace includes a rigid metal cage having spaced apart short upper lateral and medial uprights 44, 46 extending above the center of the cage, and a pair of spaced apart longer lower lateral and medial uprights 48, 50 extending below the center of the cage. A forwardly opening U-shaped posterior bar 52 is at the center of the cage, projecting to the rear of flat, wide forwardly projecting lateral and medial flanges 54, 56 at the front of the U. A pair of long upper lateral and medial pivot arms 58, 60 are pivotally secured to upper end portions of the short pair of lateral and medial uprights 44, 46, respectively. The pivot arms are pivotally connected to the short uprights by corresponding hinge joints 61 described below.

In one embodiment, the dimensions of the brace members are as follows. The short uprights extend no more than about two inches above the juncture with the flanged front portion of the brace. The long lower uprights are about four and one-half inches long. The long front arms are about seven to eight inches along from their axes of rotation.

A pair of vertically spaced apart flexible straps are affixed to the long pair of upper pivot arms 58, 60. These straps include an elongated upper strap 62 affixed near the top of the pivot arms and an intermediate strap 64 affixed to an intermediate level on the pivot arms.

A U-shaped flexible posterior strap 66 has its front ends attached to the flanged front portions 54, 56 of the cage. The posterior strap extends along the inside front face of the U-shaped brace portion 52 of the cage. Fasteners 68 releasably secure outside front end portions of the posterior strap to the outside of the flanged front portions of the cage. The U-shaped posterior strap makes a reverse bend as it wraps around the flanged front portions of the cage. The points of attachment of the posterior strap to the cage can be adjusted to shorten or lengthen the U-shaped configuration of the posterior strap to thereby adjustably control knee joint hyperextension during use.

A flexible lower leg strap 70 is attached to the lower end portions of the lower lateral and medial uprights 48 and 50. The lower leg strap provides a means for securing the lower portion of the cage to the calf region of the lower leg immediately below the knee joint.

The preferred configurations of the upper, intermediate and lower leg straps 62, 64 and 70 will now be described. The description to follow comprises one example of the presently preferred means for configuring the leg straps and arranging them on the brace to carry out functional advantages of the invention. The upper leg strap 62 is arranged to completely encircle the upper leg at about the mid-point of the thigh. The upper leg strap includes a generally U-shaped adjustable rear portion 72 rigidly affixed by a fastener 74 to the upper portion of the lateral pivot arm. The rear strap is threaded through a long narrow ring 76 carried on a top portion of the medial pivot arm. The end of the strap 72, after threading through the ring 76, is folded back on itself and releasably secured by cooperating hook and loop fasteners, such as the fastener material sold under the mark Velcro. In the illustrated embodiment, a length of hook fastener on the end of the strap portion 72 is releasably secured to a length of cooperating loop fastener on the outside of the strap. The upper leg strap 62 further includes an adjustable front portion 78 having one end rigidly affixed to an upper portion of the medial pivot arm 60 by a fastener 80. The free end of the strap 78 is threaded through a long narrow ring 82 carried on a top portion of the lateral pivot arm 58. The end of the strap 78, after threading through the ring 82, is folded back on itself with a length of hook fastener 84 at the free end of the strap 78 releasably securing to a length of cooperating loop fastener 86 on the front outside portion of the strap 78.

The intermediate strap 64 preferably serves as an anterior leg strap, wrapping around the front portion only of the patient's upper leg, between the knee joint and the upper strap 62. The intermediate strap 64 has one end rigidly affixed by a fastener 88 to an intermediate level of the medial pivot arm 60. On the opposite side of the brace, a long narrow ring 90 is rigidly affixed to the lateral pivot arm 58 by a fastener 92. The free end of the intermediate strap 64 is threaded through the ring 90 and folded back on itself to releasably secure a length of hook fastener 93 at the free end of the strap to a length of loop fastener 94 on the outside of the intermediate strap 64.

Thus, the long rotatable pivot arms 58 and 60 are releasably secured by the upper and intermediate straps 62 and 64 along about half the length of the thigh immediately above the knee joint. The adjustability of the rear strap 72 and the front strap 78 make it possible to precisely position the pivot arms 58 and 60 to the sides of the patient's upper leg.

The lower leg strap 70 preferably encircles the lower leg and includes an adjustable rear strap 96 having one end rigidly secured by a fastener 98 to the bottom portion of the lower upright 48. The lower rear strap 96 extends around the lower rear side of the brace and has its opposite free end threaded through a long narrow ring 100 affixed to the medial lower upright 50. The free end portion of the strap 96, which is threaded through the ring 100, is then folded back on itself with a length of hook fastener 102 at the free end of the strap releasably secured to a length of loop fastener 104 on the outside of the strap 96. The lower leg strap 70 further includes a front strap 106 having one end rigidly affixed by a fastener 108 to the medial lower upright 50. The front strap portion 106 extends to the lower front of the brace and has its free end threaded through a ring 108 carried on the lower portion of the lateral upright 48. The free end portion of the strap has a length of hook fastener 110 folded back and releasably secured to a length of loop fastener 112 on the front side of the lower strap 106. Thus, the lower leg strap can be adjustably secured to the lower leg spaced below the knee joint, and the separate adjustments of the rear strap 96 and the front strap 106 provide a means for precisely positioning the lower upright portions of the cage at the sides of the user's lower leg.

FIGS. 3, 4, 7 and 8 best illustrate the hinge joints 61 that rotatably secure the long pivot arms to the upper portions of the short fixed uprights at the top of the cage. The pivot joints on opposite sides of the brace are identical so only one will be described. The pivot joint includes a rigid narrow stop 114 made from a metal piece having flat sides with a pair of vertically spaced apart holes 116 extending through it. An angular top edge 118 has a circularly curved recess 120 at the front edge of the stop for receiving a noise-free bushing 122 made from a plastic material such as nylon or polypropylene. As shown best in FIG. 4, the stop 114 is mounted outside the upper fixed uprights 44 and 46, in a space between the uprights and an outer rigid metal link 124. A pair of vertically spaced apart rivets 126 on each side of the brace rigidly secure the stop 114 in the space between the link 124 and the short upper fixed lateral medial uprights 44 and 46. As shown best in the side view of FIG. 3, the lower portions of the long pivot arms 58 and 60 have an angular bottom edge 128 that makes contact with the noise-free bushing 122 of the stop 114 when each pivot arm 58 or 60 pivots to its fully upright position shown in FIG. 3. Pivot pins 130 pivotally secure the lower portions of the long pivot arms 58 and 60 to the upper outside portions of the short rigid upper lateral and medial uprights of the cage. These pivotal connections include washers 132 for smooth independent rotation of each pivot arm relative to the cage.

Figures 3, 7, 8:
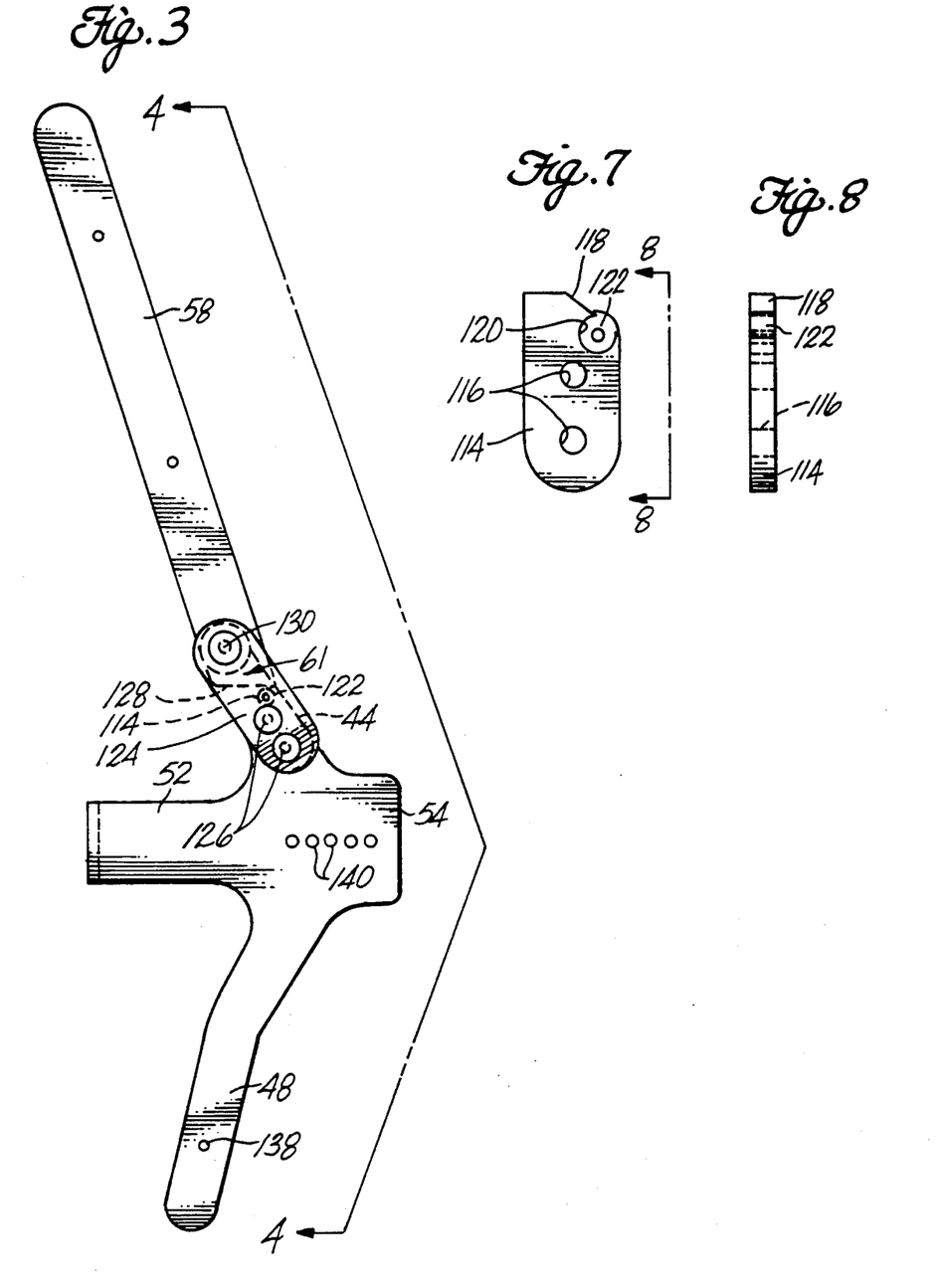
FIG. 3 is a side elevation view of a metal cage portion and a hinged pivot joint of the brace.
FIG. 7 is a side elevation view of a hinge joint bushing.
FIG. 8 is an end elevation view taken on line 8—8 of FIG. 7.
Figure 4:
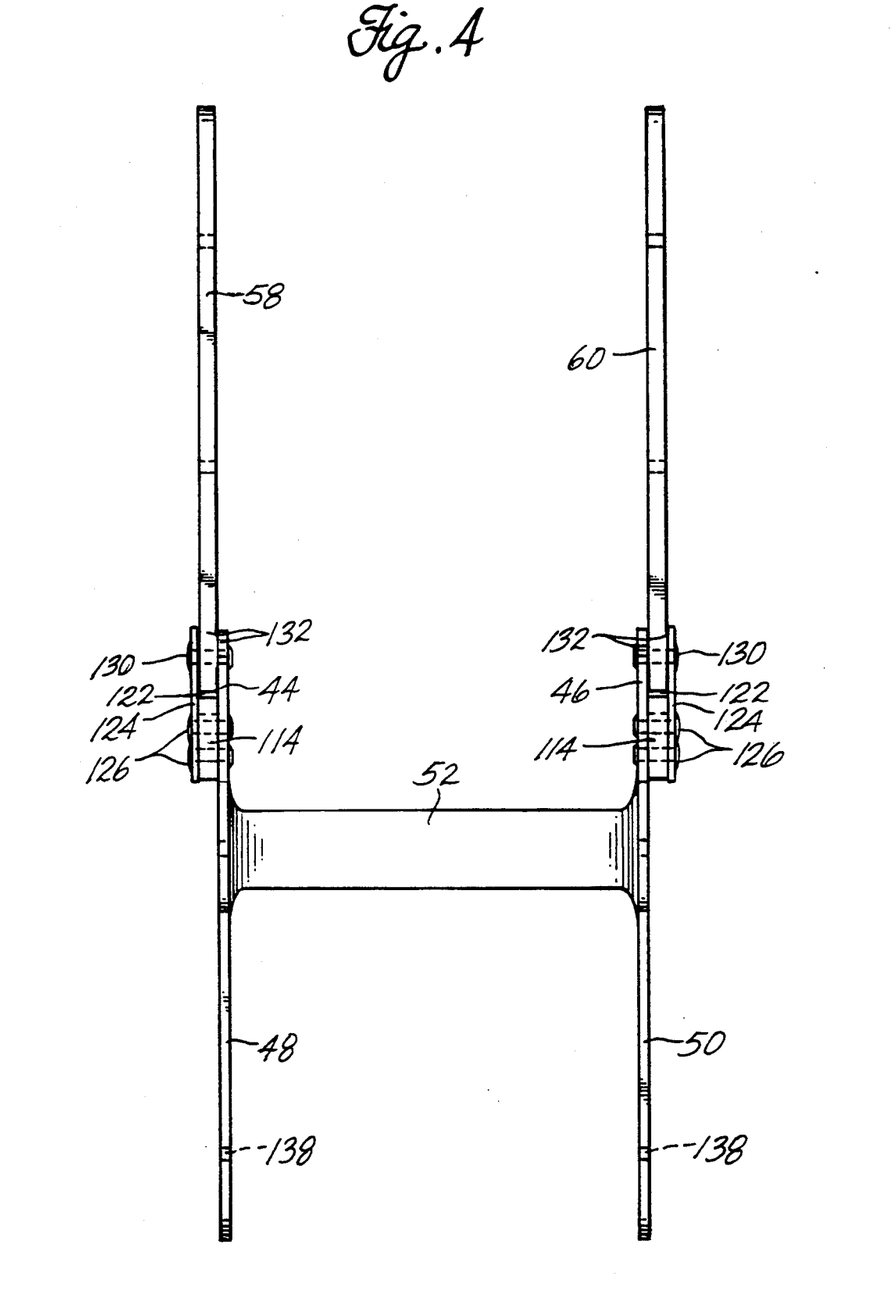
FIG. 4 is a front view of the cage and pivot joint taken on line 4—4 of FIG. 3.
Figure 5:
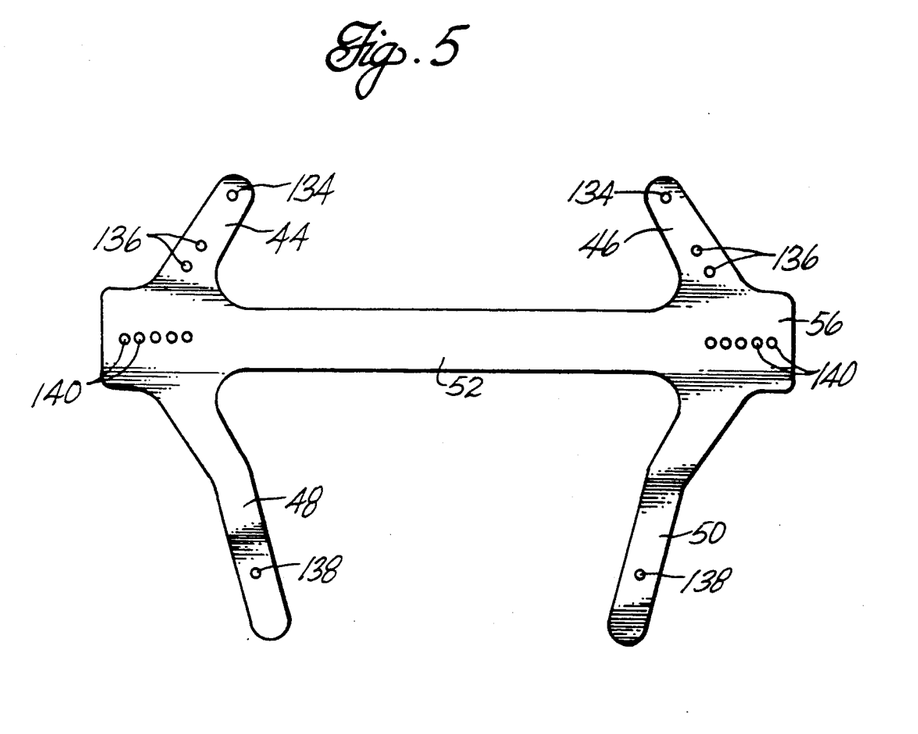
FIG. 5 is an elevation view showing the metal cage in its flat form.
Figure 6:
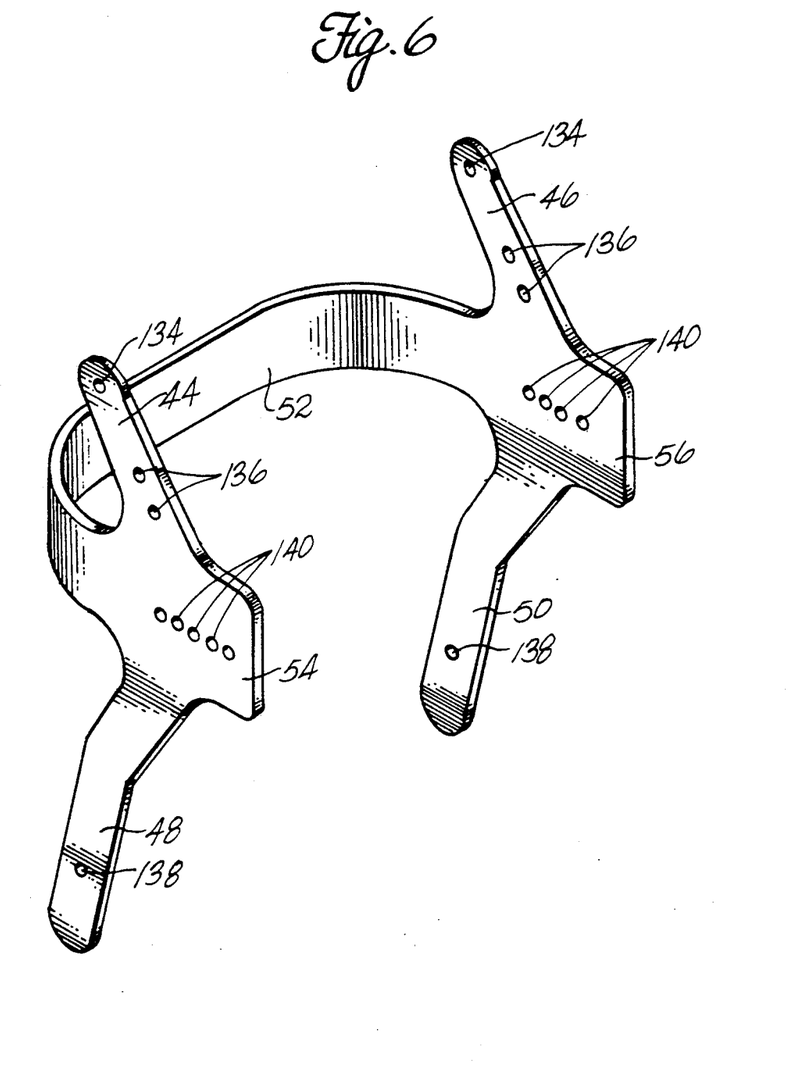
FIG. 6 is a perspective view illustrating the metal cage after it is bent into its in-use configuration.

FIGS. 5 and 6 illustrate further details of the rigid metal cage structure. FIG. 6 shows the metal cage in its flat form and FIG. 7 shows the cage in its finished form after bending of the U-shaped posterior brace portion 52 of the cage. These figures also show holes 134 at the top of the short upper lateral and medial uprights which are used for receiving the pivot pins 130 that independently pivotally secure the long pivot arms to the top of the cage. Also shown are a pair of holes 136 in each of the short fixed upper lateral and medial upright portions of the cage which are used for receiving the rivets 126 that rigidly secure the stops 114 in the space below the bottoms of the moving long pivot arms 58 and 60. Also shown are holes 138 in the lower uprights for receiving the fasteners 98 and 108 for attaching the lower leg strap 70 to the bottom of the cage. The wide flanged front portions 54 and 56 of the cage include rows of spaced apart holes 140 for receiving the screw threaded fasteners 68 for adjustably positioning the U-shaped posterior strap 66 to the middle portion of the cage. As mentioned previously, the adjustment of the fasteners 68 for the posterior strap can lengthen or shorten the posterior strap 66 so as to controllably adjust the amount of restriction to knee hyperextension during use.

Figure 9:
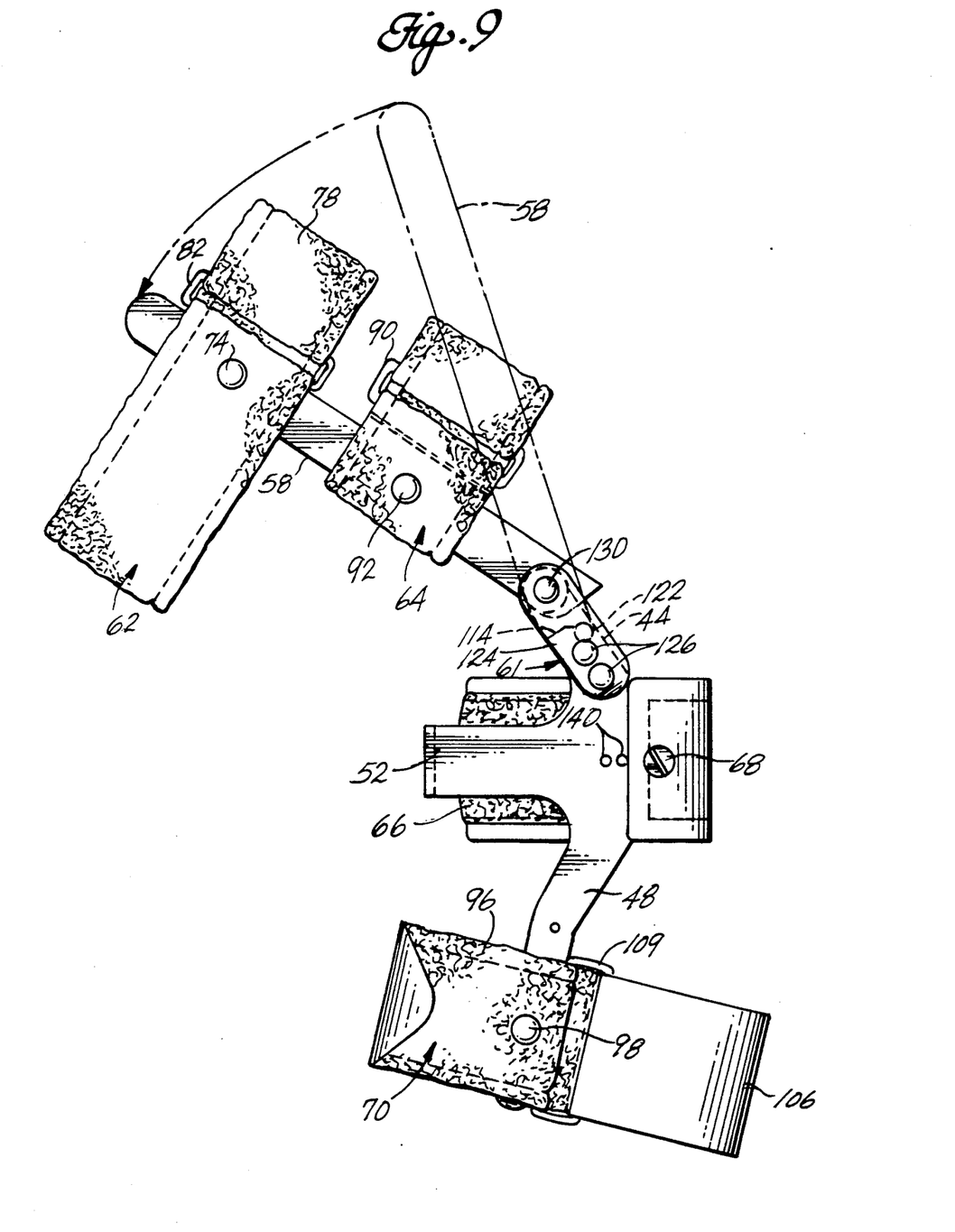
FIG. 9 is a side elevation view showing functional aspects of the new brace.
Figure 10:
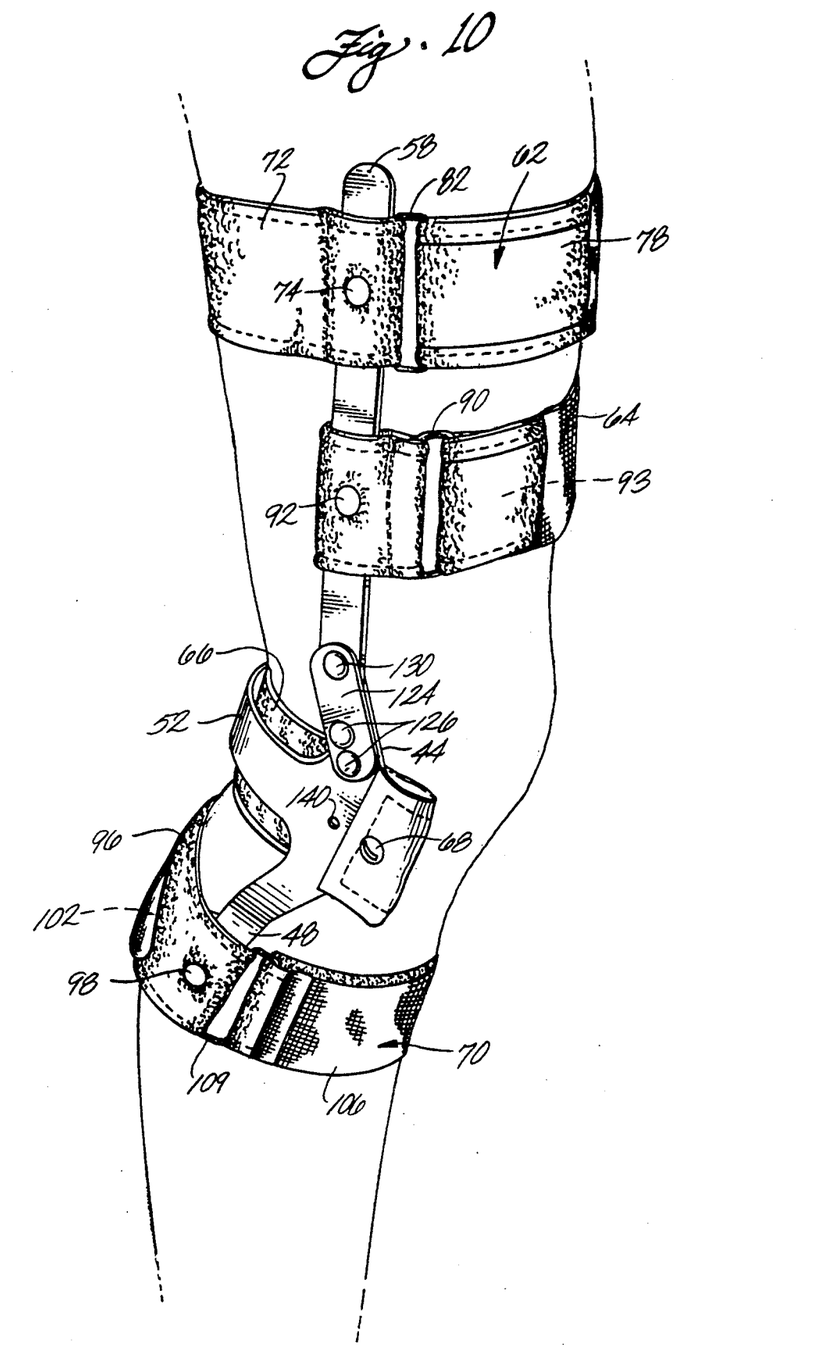
FIG. 10 is a perspective view illustrating the brace of this invention during use.

FIGS. 9 and 10 illustrate the function of the brace during use. FIG. 10 shows the brace during use attached to the knee joint of the patient in which in the upper strap 62 encircles the thigh region of the upper leg at approximately the midpoint of the thigh. The intermediate strap 64 is used as an anterior strap at an intermediate level between the upper strap 62 and the axis of the knee joint. The lower leg strap 70 is secured to an upper portion of the thigh region spaced below the knee axis of rotation. The U-shaped posterior strap 66 extends behind the knee joint at approximately the level of the knee joint axis of rotation. The sides of the cage formed by the knee brace provide a rigid means of support for the knee joint, providing a measure of mediolateral stability at the knee joint while controllably restricting knee joint hyperextension. The pivot arms 58 and 60 extend along the lateral and medial sides of the thigh immediately above the knee joint so as to provide a stable means of support on the upper leg. These long pivot arms are rigid so as to provide functional support. They also rotate with movement of the leg about the knee joint, as shown in FIG. 9, so as to constantly track the knee motion during use. By providing upper and intermediate level flexible leg straps as a means of support for the long rigid pivot arms, the thigh forces that are developed during use are effectively distributed across the lower portion of the thigh during use. The lower portions of the pivot arms are pivotally secured to the short rigid uprights 44 and 46 of the cage, and as a result, the height of the cage structure above the level of the knee joint is limited. During use, the rigid cage structure does not extend above the level of the knee. Thus, when the patient sits, the knee brace is unobtrusive, and the cage structure does not protrude in an unnatural looking way from the inside of the patient's clothes. The stops 114 within each hinge joint 61 limit forward rotation of the upper pivot arms 58 and 60 so that hyperextension is restricted. The plastic bushing 122 on each stop provides noise-free operation during use.

Thus, the hinged knee cage type brace efficiently controls knee joint hyperextension while allowing a more normal gait and comfortable sitting position. The hinged joints accurately track the natural motion of the knee. The knee brace is firmly held in position on the patient's leg and the hinged upper portion of the brace provides functional stability during use.

What is claimed is:

1. A cage-type knee brace comprising a rigid cage for fitting around opposite sides of the knee joint and having a generally U-shaped posterior brace portion for extending around the sides of and behind the knee joint, a pair of short upper lateral and medial uprights rigidly joined with opposite front portions of the U-shaped posterior brace for extending upwardly a short distance along lateral and medial sides of the upper leg above the knee joint, and a pair of lower lateral and medial uprights rigidly joined with opposite front portions of the U-shaped brace for extending downwardly along lateral and medial sides of the lower leg below the knee joint, the lower pair of uprights being longer in length than the short upper lateral and medial uprights;

a pair of elongated rigid lateral and medial pivot arms pivotally affixed to end portions of the short upper lateral and medial uprights at pivot points spaced above the U-shaped posterior brace portion of the cage;

means for pivotally securing the lower ends of the pivot arms to the pivot points on the short uprights of the cage so the pivot arms can each rotate independently of each other relative to the cage, the pivot arms extending along lateral and medial sides of the upper leg above the knee joint when the cage is positioned around the knee joint;

separate stop means rigidly affixed to the short upper lateral and medial uprights for engaging lower portions of corresponding pivot arms to restrict forward rotation of each pivot arm relative to the cage and to allow independent rotation of each pivot arm in a rear direction relative to the cage;

a flexible lower leg strap secured to the lower lateral and medial uprights for releasably securing a lower portion of the cage to the lower leg below the knee joint;

a flexible U-shaped posterior strap affixed to the front portions of the U-shaped posterior brace and extending inside the U-shaped posterior brace for contacting a posterior portion of the knee joint when the cage is positioned around the knee joint; and one or more flexible U-shaped upper leg straps secured to the long pivot arms for releasably securing the pivot arms to the lateral and medial sides of the upper leg, the pivot arms being independently rotatable about their axes of rotation through the pivot points on the cage and extending for a distance of at least about one half the length of the thigh region of the leg to function by distributing thigh forces during a walking gait while the U-shaped posterior strap is held in a fixed position behind the knee joint to restrict hyperextension of the knee joint.

2. Apparatus according to claim 1 in which the long pivot arms each have a length substantially longer than each of the lower uprights.

3. Apparatus according to claim 1 in which each stop includes a noise-free bushing for contact with a lower end portion of the pivot arm to provide a noise-free stop against further forward rotation of the pivot arm.

4. Apparatus according to claim 3 in which each noise-free bushing is made from a plastic material which can be removed from the stop and replaced.

5. Apparatus according to claim 1 in which the upper leg strap means for securing the pivot arms to the upper leg comprise a flexible upper leg strap secured to upper end portions of the pivot arms for releasably securing the pivot arms to the upper leg, and a flexible intermediate leg strap secured to the pivot arms between the upper leg strap and the pivot axis of the pivot arms for releasably securing intermediate portions of the pivot arms to the upper leg.

6. Apparatus according to claim 5 in which the upper leg strap comprises a combination of a posterior strap portion adjustable in length for extending around the rear side of the patient's upper leg, and an anterior strap portion of adjustable length for extending around a front portion of the patient's upper leg, the two straps combining to encircle the upper leg to adjustably position the lateral and medial pivot arms at the sides of the upper leg.

7. Apparatus according to claim 6 in which the lower leg strap includes a combination lower posterior strap of adjustable length for extending around rear portion of the patient's lower leg, and an adjustable lower anterior strap of adjustable length for extending around a front portion of the patient's lower leg, the two straps combining encircle the lower leg and adjustably position the lower uprights at the lateral and medial sides of the lower leg.

8. Apparatus according to claim 8 in which the intermediate strap comprises at least an intermediate anterior flexible strap of adjustable length for extending around a front intermediate portion of the patient's upper leg above the knee joint.

9. Apparatus according to claim 9 in which the stop means include plastic bushing inserts for contacting the bottom portions of the rotatable pivot arms with noise-free contact.

* * * * *

UNITED STATES PATENT AND TRADEMARK OFFICE
CERTIFICATE OF CORRECTION

PATENT NO. : 5,207,637
DATED : May 4, 1993
INVENTOR(S) : Wayne R. Janke; Dan J. Edwards It is certified that error appears in the above-identified patent and that said Letters Patent is hereby corrected as shown below:

ON THE TITLE PAGE:

Abstract, line 10, change "intermedi7" to -- intermedi- --.

Column 2, line 26, change "hypertension" to -- hyperextension --.

Column 3, line 27, change "forth" to -- fourth --.

Column 4, line 25, after 'along" delete "from".

Column 6, line 46, after "which" delete "in".

Column 8, line 46, after "around" insert -- a --.
Column 8, line 50, after "combining" insert -- to --.

Signed and Sealed this

Twenty-second Day of February, 1994

Attest:

BRUCE LEHMAN

Attesting Officer     Commissioner of Patents and Trademarks